US00PP18757P2

(12) United States Plant Patent
Talmadge

(10) Patent No.: US PP18,757 P2
(45) Date of Patent: Apr. 22, 2008

(54) *DIASCIA* PLANT NAMED 'BALWINLAMP'

(50) Latin Name: *Diascia×hybrida*
Varietal Denomination: Baldwinlamp

(75) Inventor: Paul A. Talmadge, Orcutt, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 11/602,631

(22) Filed: Nov. 20, 2006

(51) Int. Cl.
*A01H 5/00* (2006.01)

(52) U.S. Cl. ..... Plt./263
(58) Field of Classification Search ..... Plt./263
See application file for complete search history.

*Primary Examiner*—Kent Bell
*Assistant Examiner*—June Hwu
(74) *Attorney, Agent, or Firm*—Audrey Charles

(57) ABSTRACT

A new and distinct cultivar of *Diascia* plant named 'Balwinlamp', characterized by its light pink-colored flowers, medium green-colored foliage, and moderately vigorous, semi-upright growth habit.

1 Drawing Sheet

Latin name of genus and species of plant claimed: *Diascia×hybrida.*
Variety denomination: 'Balwinlamp'.

BACKGROUND OF THE INVENTION

The present invention relates to a new and distinct cultivar of *Diascia* plant botanically known as *Diascia×hybrida* and hereinafter referred to by the cultivar name 'Balwinlamp'.

The new cultivar originated in a controlled breeding program in Guadalupe, Calif. during September 2003. The objective of the breeding program was the development of *Diascia* cultivars that continuously flower with medium green-colored foliage and a well-branched, upright growth habit.

The new *Diascia* cultivar is the result of cross-pollination. The female (seed) parent of the new cultivar is the proprietary *Diascia×hybrida* breeding selection designated DZPJXXG-M, not patented, characterized by its medium pink-colored flowers, medium green-colored foliage, and upright growth habit. The male (pollen) parent of the new cultivar is the proprietary *Diascia×hybrida* breeding selection designated JHWWPLJ-M, not patented, characterized by its light pink-colored flowers, medium green-colored foliage, and upright growth habit. The new cultivar was discovered and selected as a single flowering plant within the progeny of the above stated cross-pollination during March 2004 in a controlled environment at Guadalupe, Calif.

Asexual reproduction of the new cultivar by terminal stem cuttings since March 2004 at Guadalupe, Calif., Arroyo Grande, Calif., and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balwinlamp' as a new and distinct cultivar of *Diascia* plant:

1. Light pink-colored flowers;
2. Medium green-colored foliage; and

3. Moderately vigorous, semi-upright growth habit.

Plants of the new cultivar differ from plants of the female parent primarily in flower color and growth habit and from plants of the male parent primarily in growth habit.

Of the many commercially available *Diascia* cultivars known to the inventor, the most similar in comparison to the new cultivar is WINK Lavender Pink 'Balwinlapi', not patented. However, in side by side comparisons, plants of the new cultivar differ from plants of 'Balwinlapi' in the following characteristics:

1. Plants of the new cultivar have more inflorescences than plants of 'Balwinlapi'; and
2. Plants of the new cultivar have a flower color different from plants of 'Balwinlapi'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balwinlamp'. The plants were grown in 4.5 inch pots for 6 weeks in a greenhouse at West Chicago, Ill.

DETAILED BOTANICAL DESCRIPTION

Figure 1:
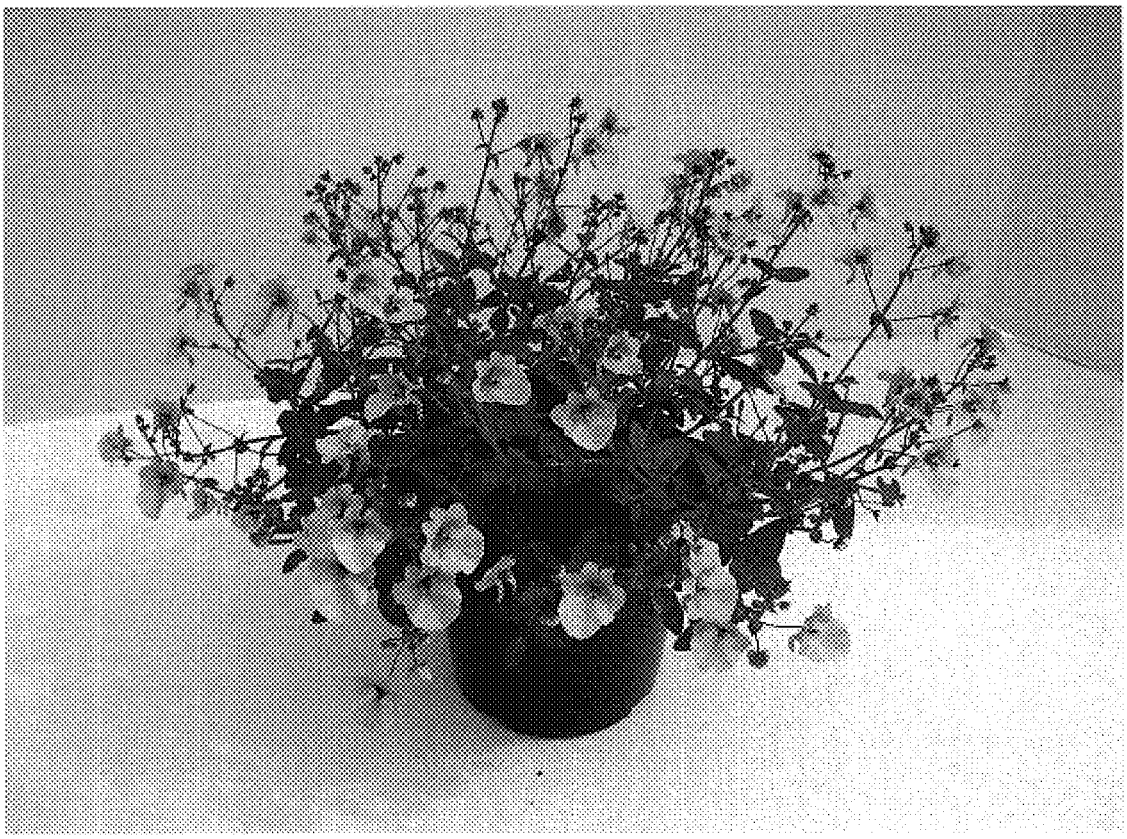
FIG. 1 illustrates a side view of the overall growth and flowering habit of 'Balwinlamp'.
Figure 2:
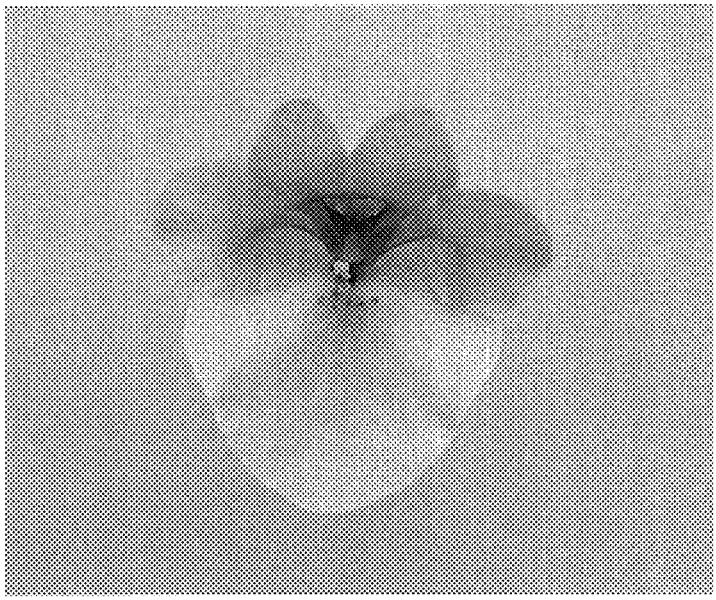
FIG. 2 illustrates a close-up view of an individual flower of 'Balwinlamp'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on May 1, 2006 between 1:00 p.m. and 3:00 p.m. under natural light conditions in West Chicago, Ill.

The following descriptions and measurements describe plants produced from cuttings taken from stock plants and grown in a glass-covered greenhouse under conditions comparable to those used in commercial practice. The plants were grown at West Chicago, Ill. in 4.5 inch pots for 6 weeks utilizing a soilless growth medium. Greenhouse temperatures were maintained at approximately 70° F. to 77° F. (21° C. to 25° C. during the day and approximately 65° F. to 68° F. (18° C. to 20° C.) during the night Greenhouse light levels of 2,500 footcandles to 6,000 footcandles were maintained during the day.

Botanical classification: *Diascia×hybrida* cultivar Balwinlamp.

Parentage:

*Female parent.*—Proprietary *Diascia×hybrida* breeding selection designated DZPJXXG-M, not patented.

*Male parent.*—Proprietary *Diascia×hybrida* breeding selection designated JHWWPLJ-M, not patented.

Propagation:

*Type cutting.*—Terminal stem.

*Time to initiate roots.*—Approximately 6 to 9 days.

*Time to produce a rooted cutting.*—Approximately 21 to 24 days.

*Root description.*—Fine, fibrous.

*Rooting habit.*—Freely branching.

Plant description:

*Commercial crop time.*—Approximately 5 to 7 weeks from a rooted cutting.

*Growth habit and general appearance.*—Moderately vigorous, semi-upright.

*Size.*—Height from soil level to top of plant plane: Approximately 15.4 cm. Width: Approximately 26.7 cm.

*Branching habit.*—Freely branching. Quantity of main branches per plant: Approximately 7.

*Branch.*—Shape: Square: Strength: Strong. Length: Approximately 15.0 cm. Diameter: Approximately 2.0 mm. Length of central internode: Approximately 2.3 cm. Texture: Sparsely glandular pubescent. Gland color: Colorless. Color of young and mature stems: 144A.

Foliage description:

*General description.*—Quantity of leaves per main branch: Approximately 8. Fragrance: None. Form: Simple. Arrangement: Opposite.

*Leaves.*—Aspect: Perpendicular to stem. Shape: Deltoid. Margin: Serrate. Apex: Acute. Base: Truncate. Venation pattern: Pinnate. Length of mature leaf: Approximately 2.8 cm. Width of mature leaf: Approximately 1.8 cm. Texture of upper surface: Glabrous. Texture of lower surface: Sparsely glandular pubescent on midvein. Gland color: Colorless. Color of upper surface of young foliage: 137C with venation of 144C. Color of lower surface of young foliage: 191B with venation of 144C. Color of upper surface of mature foliage: 137A with venation of 144C. Color of lower surface of mature foliage: Between 191C and 191B with venation of 144C.

*Petiole.*—Length: Approximately 3.2 mm. Diameter: Approximately 1.0 mm. Texture: Sparsely glandular pubescent. Gland color: Colorless. Color: 144B.

Flowering description:

*Flowering habit.*—'Balwinlamp' is freely flowering under outdoor growing conditions with substantially continuous blooming from spring through autumn and year-round in greenhouse environment.

*Lastingness of individual flower on the plant.*—Approximately 3 to 4 days.

Inflorescence description:

*General description.*—Type: Terminal raceme. Quantity per plant: Approximately 22. Fragrance: None. Length or height: Approximately 6.2 cm. Width: Approximately 5.5 cm. Quantity of fully open flowers per inflorescence: Approximately 4.

*Peduncle.*—Shape: Square in cross section. Strength: Strong. Aspect: Erect. Length: Approximately 3.0 cm. Diameter: Approximately 1.5 mm. Texture: Glandular pubescent. Gland color: Colorless. Color: 144A.

Flower Description:

*Type.*—solitary, zygomorphic.

*Bud.*—Rate of opening: Generally takes 2 to 3 days for bud to progress from first color to fully open flower.

*Bud just before opening.*—Shape: Ovoid. Length: Approximately 3.2 mm. Width. Approximately 2.4 mm. Depth: Approximately 3.2 mm. Texture: Glandular pubescent. Gland color: 93A. Color: 157A.

*Corolla.*—Shape: Obovate. Width: Approximately 1.8 cm. Length: Approximately 1.9 cm. Depth: Approximately 6.8 mm.

*Petals.*—Quantity: 5 modified petals fused at base with 2 upper petals, 2 lateral petals, and one larger lower lip petal. The base of the lateral petals modified into sharply curved nectar spurs. Shape: Obovate, lower petal convex. Appearance: Iridescent. Margin: Entire. Apex: Obtuse. Length of upper petals: Approximately 9.0 mm. Width of upper petals: Approximately 5.0 mm. Length of upper petal indentation at base: Approximately 3.0 mm. Width of upper petal indentation at base: Approximately 4.0 mm. Length of lateral petals: Approximately 9.4 mm. Width of lateral petals: Approximately 6.2 mm. Length of lower petal: Approximately 1.3 cm. Width of lower petal: Approximately 1.7 cm. Texture of upper surface: Glabrous with sparse sessile glands at the base of the lower petal. Gland color: N78A. Texture of lower surface: Sparsely glandular pubescent. Gland color: 93A. Color of upper surface when fully open: all petals 84C except upper petals having petal base of N78B and indentation of 2A. Color of lower surface when fully open: all petals 84D except upper and lateral petals having petal base of 85B and upper petal indentation of 2D with spots of N92A.

*Nectar spur.*—Quantity: 2 per flower. Length: Approximately 6.8 mm. Diameter at tip: Approximately 1.0 mm. Diameter at base: Approximately 3.0 mm. Texture of inner and outer surfaces: Glabrous. Color of outer surface: 85D with streaks of 85B at the tips.

*Calyx.*—Shape: Star. Diameter: Approximately 5.8 mm.

*Sepals.*—Quantity per flower: 5, fused at base. Shape: Lanceolate. Apex: Acute. Length: Approximately 3.0 mm. Width: Approximately 1.0 mm. Texture of upper surface: Glabrous. Texture of lower surface: Sparsely glandular pubescent. Gland color: Mixture of colorless and 93A. Color of upper and lower surfaces: 144A.

*Pedicel.*—Strength: Strong. Aspect: Acute angle to stem. Length: Approximately 2.0 cm. Diameter: Less than 1 mm. Texture: Sparsely glandular pubescent. Gland color: Mixture of colorless and 93A. Color: 144A with faint overlay of 187A.

*Reproductive organs.*—Androecium: Stamen quantity: 4 per flower. Filament length: Approximately 2.0 mm. Filament texture: Sparsely glandular pubescent. Gland color: 93A. Filament color: N78B transitioning to 84C at base. Anther shape: Bilobed. Anther length: Approximately 1.0 mm. Anther color: 4B. Pollen amount: Abundant. Pollen color: 2A. Gynoecium: Pistil quantity: 1 per flower. Pistil length: Approximately 4.0 mm. Stigma shape: Round. Stigma length: Less than 1 mm. Stigma color: Colorless, opaque. Style length: Approximately 2.0 mm. Style color: 144D. Ovary diameter: Approximately 1.5 mm. Ovary texture: Glabrous. Ovary color: N144C.

Seed and fruit production: Neither seed not fruit production has been observed.

Disease and pest resistance: Resistance to pathogens and pests common to *Diascia* has not been observed.

What is claimed is:

1. A new and distinct cultivar of *Diascia* plant named 'Balwinlamp', substantially as herein shown and described.

* * * * *